(12) United States Patent
Taylor

(10) Patent No.: US 7,747,408 B2
(45) Date of Patent: Jun. 29, 2010

(54) METHOD OF SCANNING

(75) Inventor: David William Taylor, Dursley (GB)

(73) Assignee: Renishaw PLC, Wotton-under-Edge (GB)

( * ) Notice: Subject to any disclaimer, the term of this patent is extended or adjusted under 35 U.S.C. 154(b) by 413 days.

(21) Appl. No.: 10/577,855

(22) PCT Filed: Nov. 4, 2004

(86) PCT No.: PCT/GB2004/004664

§ 371 (c)(1),
(2), (4) Date: Apr. 28, 2006

(87) PCT Pub. No.: WO2005/047818

PCT Pub. Date: May 26, 2005

(65) Prior Publication Data

US 2007/0145265 A1    Jun. 28, 2007

(30) Foreign Application Priority Data

Nov. 5, 2003    (GB) .................................. 0325803.5

(51) Int. Cl.
*G01C 9/00* (2006.01)
(52) U.S. Cl. .................................................. 702/150
(58) Field of Classification Search .................. 702/150
See application file for complete search history.

(56) References Cited

U.S. PATENT DOCUMENTS

| | | | |
|---|---|---|---|
| 5,391,871 A | 2/1995 | Matsuda et al. | |
| 5,440,496 A | 8/1995 | Andersson et al. | |
| 6,327,788 B1* | 12/2001 | Seddon et al. | 33/551 |
| 6,697,096 B2* | 2/2004 | Agorio | 347/261 |
| 7,436,522 B2* | 10/2008 | Steinbichler et al. | 356/601 |
| 2005/0060868 A1* | 3/2005 | McMurtry | 29/559 |
| 2006/0037208 A1* | 2/2006 | McMurtry | 33/554 |

FOREIGN PATENT DOCUMENTS

| | | |
|---|---|---|
| EP | 0 517 270 A2 | 12/1992 |
| JP | A-02-147803 | 6/1990 |
| WO | WO 03/046412 A1 | 6/2003 |
| WO | WO 2004/020939 A2 | 3/2004 |

\* cited by examiner

*Primary Examiner*—Aditya Bhat
(74) *Attorney, Agent, or Firm*—Oliff & Berridge, PLC

(57) ABSTRACT

A method of scanning is disclosed comprising, providing a scanning system (10) having a sample holder (14) and a relatively movable scanning device (18), performing a scan of at least a part of an object (22) located on the sample holder (14), establishing orientation of the sample holder and interpreting data from a scan using the orientation whereby, the orientation is established using data from the scan of the surface of the sample holder. The orientation may be established by defining a plane (56*b*) of the sample holder, which may be limited by boundaries (76*a*, 76*b*).

12 Claims, 5 Drawing Sheets

METHOD OF SCANNING

This invention relates to a method of scanning.

BACKGROUND

When a rotatable sample holder is used in conjunction with a relatively movable scanning device, it is known to scan around the holder in order to establish or confirm the radius of the holder and the co-ordinates of the origin of the holder. This information is used to interpret data produced during the scanning of an object located on the sample holder.

A problem with this method is that it assumes that the sample holder surfaces are square and that the axis of the circumferential surface of the sample holder remains co-linear with respect to its rotational axis along its length i.e. that the surface of the sample holder on which a sample is located is perpendicular to the rotational axis. Additionally, in order for this assumption to be treated as valid, the equipment must be manufactured to tight tolerances which increases the cost of the equipment.

An alternative scanning system uses Cartesian scanning in which case the sample holder is stationary during a scan. Traditionally it is assumed that the centre line of the sample holder is square to the axes of the scanning system however, for certain applications where it is important that the longitudinal axis of a sample is known this assumption may be invalid leading to errors.

SUMMARY

Accordingly, according to one aspect the invention provides a method of scanning comprising the steps of:
providing a scanning system having a sample holder and a relatively movable scanning device;
performing a scan of at least a part of an object located on the sample holder;
establishing orientation of the sample holder; and
interpreting data from the scan using the orientation of the sample holder characterised in that, the orientation is established using data from the scan of the object.

Preferably, the sample holder rotates about a rotational axis and the orientation of the sample holder is established with respect to the rotational axis. Alternatively, the sample holder is stationary during a scan. Establishing the orientation of the sample holder provides a datum for the sample scan.

Preferably, the orientation is established by defining a plane of the sample holder.

According to a second aspect, the invention provides a method of scanning comprising the steps of:
providing a scanning system having a sample holder and a relatively movable scanning device;
scanning a datum;
scanning a sample; and
interpreting data from the sample scan using data from the datum scan
characterised in that the scanning system automatically carries out the datum and sample scans.

Once the scanning system recognises that a sample is located on the sample holder, the process is automated so does not require operator intervention. The system may recognise location of a sample due to an operator informing it, for example by pushing a button, or, by sensing that a sample is located. Such sensing includes a contact being correctly made between the sample holder and scanning system, the weight of a sample being present or the breaking of a light beam within the sample envelope of the scanning system.

According to a third aspect, the invention provides a method of scanning comprising the steps of:
providing a scanning system having a sample holder and a relatively movable scanning device;
scanning a datum;
scanning a sample; and
interpreting data from the sample scan using data from the datum scan
characterised in that both the datum and sample scans are carried out effectively as one scan.

The advantage of this is that the system does not require operator involvement. The datum and sample scans can be carried out as a single scan i.e. with continuous motion, or at the completion of one of the scans, the probe may pause before starting the next one. This enables the data from the two scans to be separated without an operator having to determine where the split occurs so reduces the chance of errors occurring.

The two scans (or parts of a single scan) can be carried out in either order.

The probe does not require re-positioning between the two scans when a pause is included.

BRIEF DESCRIPTION OF DRAWING

The invention will now be described by way of example, with reference to the accompanying drawings, of which.

DETAILED DESCRIPTION

Figure 1:
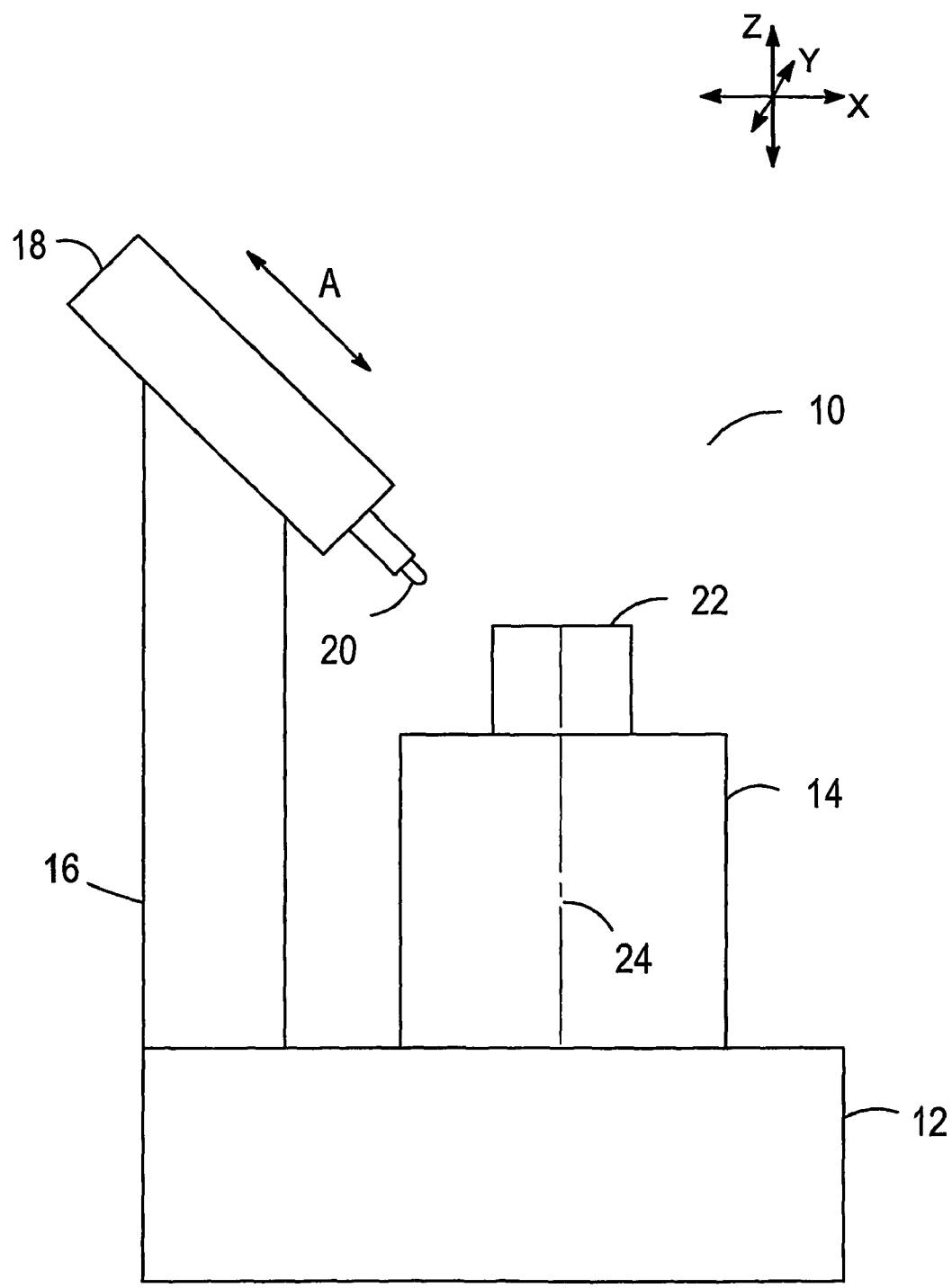
FIG. 1 shows schematically a scanning system.

FIG. 1 shows a scanning system 10 having a base 12 which supports a sample holder 14 and a back portion 16. A scanning device 18, which in this case is a probe having a scanning tip 20, is supported by the back portion 16. A sample 22 is located on the sample holder 14 for scanning. The sample holder 14 is moveable along a vertical or Z-axis and is rotatable about an axis 24 which is substantially parallel to the vertical motion. Thus, the sample holder 14 moves along a helical path. The probe tip 20 is moveable along an axis A which is disposed at 45° to the axis of rotation 24 of the sample holder 14.

In an alternative arrangement, the sample holder 14 is rotatable and the scanning device moves in the vertical or Z direction.

Figure 2:
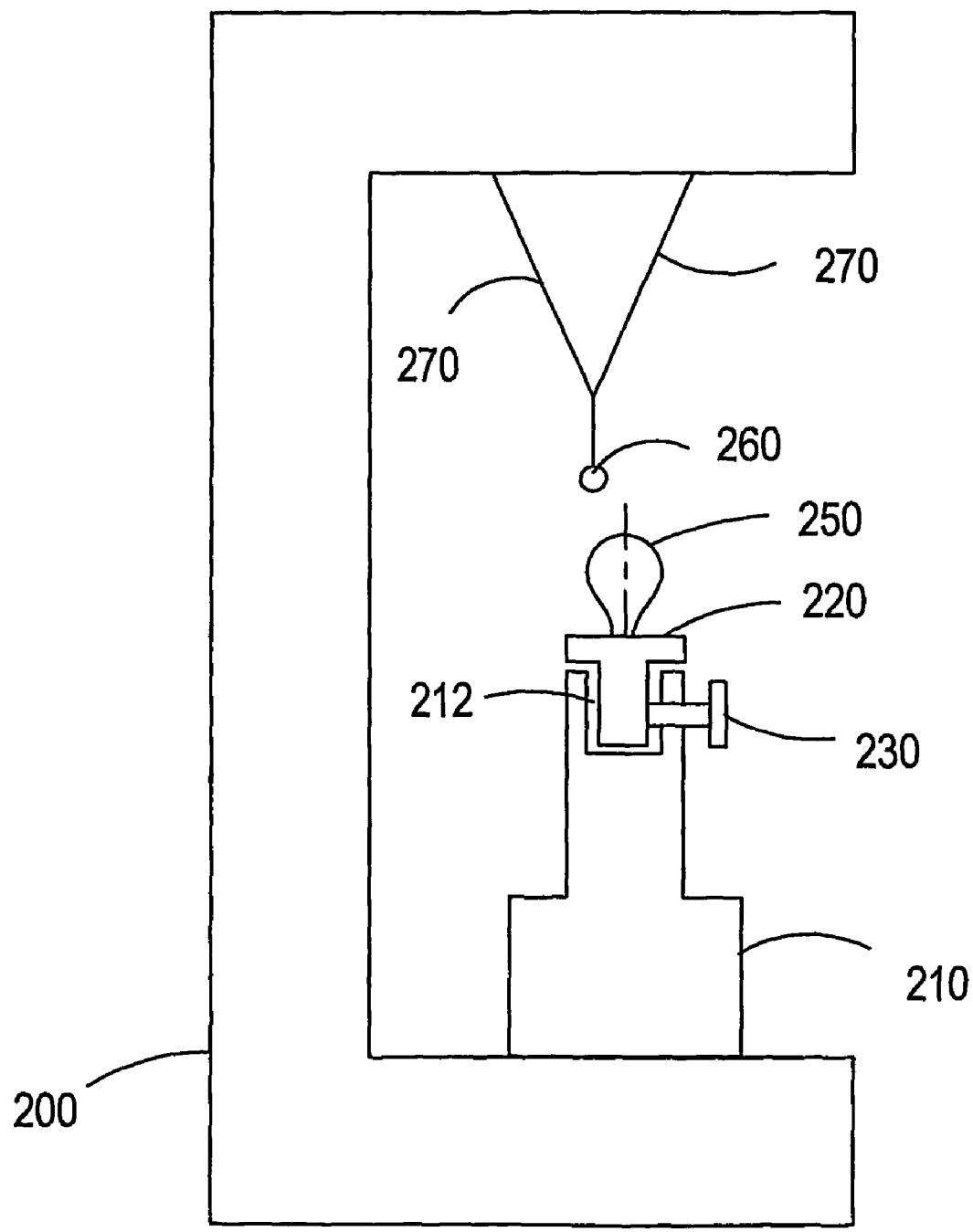
FIG. 2 shows schematically an alternative scanning system.

FIG. 2 shows an alternative scanning system having a c-shaped frame 200 onto which a sample mount 210 is placed. At the distal end of the sample mount 210 is an opening 212 designed to receive a sample holder 220. The sample holder 220 is secured to the sample mount 210, for the purposes of scanning a sample 250, using a screw 230. A probe 260 extends down from the frame 200 towards a sample 250 via adjustable struts 270.

In this example, the sample mount 210 is fixed and the probe 260 moves around the sample. One way to scan a sample is to carry out a series of radial line scans vertically along the sample.

The Cartesian scanning system described with respect to FIG. 2 may alternatively be used to conduct a spiral scan of a sample.

Figure 3:
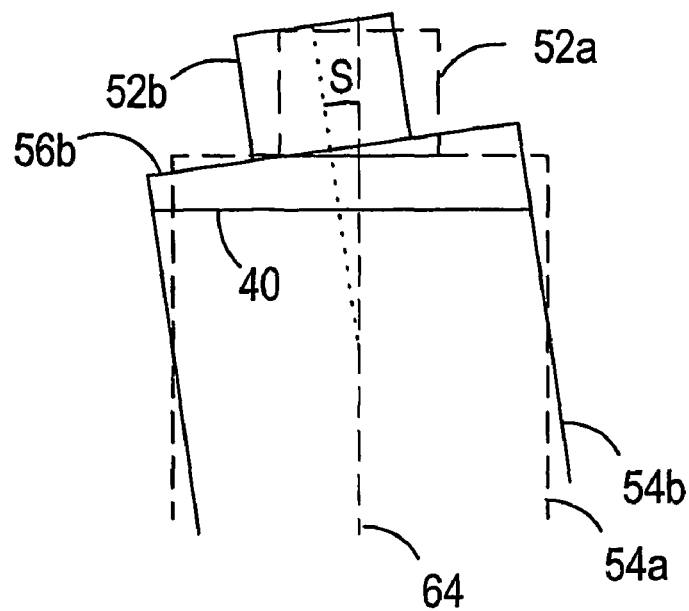
FIG. 3 shows schematically the effect of an orientation of a sample holder with respect to the rotatable axis.

FIG. 3 shows the effect of a misaligned or non co-linear sample holder 54b. Instead of lying co-linearly with respect to the rotatable or vertical axis 64 as shown by dotted lines designated 54a and 52a, a misaligned sample holder 54b is at an angle, the swash angle S, with respect to the rotational or vertical axis 64. This in turn means that a scan of a sample 52b located on the misaligned sample holder 54b will obtain distorted results as, traditionally when interpreting the scan data, it is assumed that the sample holder is co-linear with respect to the rotational or vertical axis 64.

To remove this source of error, the orientation of the plane of the upper surface 56b of the sample holder 54b is established. Advantageously, according to the invention, this is achieved by extracting data which meets certain requirements from the data set of a scan of an object. This requires the scan of an object to include probing of at least a portion of the surface of the sample holder on which the sample is located.

In the simplest case, where the sample holder is stationary or merely rotates, this can be achieved by extracting three angularly spaced apart measurements of the upper surface 56b of the sample holder.

Preferably, three equidistanced angularly spaced apart measurements are taken. These three points define the plane of the upper surface 56b and can be used to interpret or correct data relating to the sample to reflect the real plane of the upper surface 56b. It is preferred that the plane orientation is obtained by using a plurality of data points as this reduces the effect of surface defects.

Referring now to FIG. 1, when the sample holder 14 is assigned a vertical movement as well as a rotational movement, more than three points are required as the helical or spiral path through which the sample holder moves will mask the actual plane of the upper surface 26b. In this situation, a number of points are taken encompassing at least two-thirds of a rotation of the sample holder. Two-thirds of a revolution is the minimum angular rotation required to define a plane accurately.

In the embodiment where the sample holder does not rotate, it is also preferred that data is extracted for at least 240° (or two thirds) around the surface of the sample holder.

The size of the upper surface of the sample holder is a further factor which determines the size of the orientation data set. If the upper surface is small, it is preferred that a larger number of data points are taken as this then reduces the error introduced by any surface defects.

Figure 4:
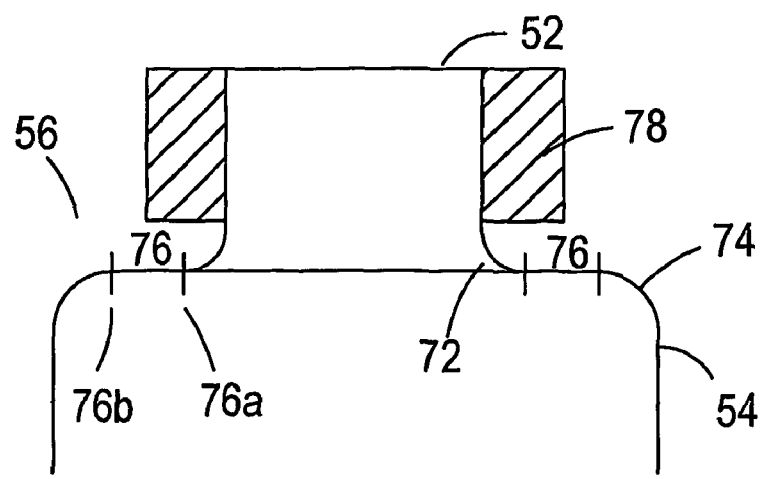
FIG. 4 shows a preferred method of scanning.

Referring now to FIG. 4, it is important that the probe tip is located properly on the upper surface 56 when data for the orientation information is being extracted so that any edge effects are not included. For example, if the sample holder 54 is provided with a chamfer 74 and the sample 52 has a rounded edge 72 where it meets the sample holder 54. If either the chamfer 74 or rounded edge 72 are included when the plane of the upper surface is being calculated, errors would be introduced. Thus, in a preferred embodiment, inner and outer radial boundaries are set which define a region from which the orientation data must be taken.

The boundaries are also established by extracting data from the sample scan. Data from one revolution around the circumference of the sample holder is used to establish the radius and co-ordinates of the origin of the sample holder. A minimum of at least three, but preferably four or more measurements are extracted.

A known defect in the surface, for example, the chamfer 74, is subtracted from the radius of the sample holder 54 to create the outer boundary 76b. The radius of the sample 52 plus rounded edge 72 is added to the origin of the sample holder 54 to create the inner boundary 76a. A safety factor, for example, to account for non-central placement of the sample may also be added to or subtracted from the boundaries. The probe tip thus has a defined region 76 in which the orientation information must be collected in order to be considered viable.

As the orientation information is extracted from a scan of a sample, there is a chance of interference if, for example, the sample includes an overhang 78. In this situation, the probe tip may encounter the sample overhang 78 instead of the upper surface of the sample holder 54. To alleviate this problem, the orientation information may be further constricted by a z boundary which defines limits for the extraction of data in the vertical direction.

For the scanning system of FIG. 2, the z boundary does not need to be established for a particular sample holder and mount combination as their height is known and does not change appreciably from one scan to the next so, this information is used to set a z boundary, if required.

For the scanning system of FIG. 1, where a sample holder may move vertically it is required to set a z boundary for each scan. As the probe scans 40 perpendicularly to the rotational or vertical axis 64 (see FIG. 3), it is assumed that the probe tip will first encounter the upper surface 56 of the sample holder 54b at the lowest point on the plane surface. This point of first encounter is used to define z boundaries for the orientation scan. As a minimum of between two-thirds and about three-quarters (see FIG. 5) of a revolution is desired to define the plane of the upper surface, the upper vertical distance is defined as a minimum of the height change experienced during one revolution. The lower vertical distance is preferably defined not as zero, but as minus about half a revolution to account for circumstances where the swash angle S is small when the assumption that the first encounter is at the lowest point may not be valid. Again additional safety factors may be added to these limits.

When a z boundary has been defined, it has the effect of limiting the swash angle S that can be detected. Note, a system has a maximum swash angle with which it can function and this provides a maximum value that the z boundary cannot exceed. This can be advantageous as, the larger the swash angle S, the more eccentric the movement of the sample which can introduce additional errors into a scan. For example, when a touch probe is used, there are limits to the amount of motion the probe tip can undergo along its axis (FIG. 1, axis A). When the probe nears the limits of this motion, accuracy is reduced.

Figure 5:
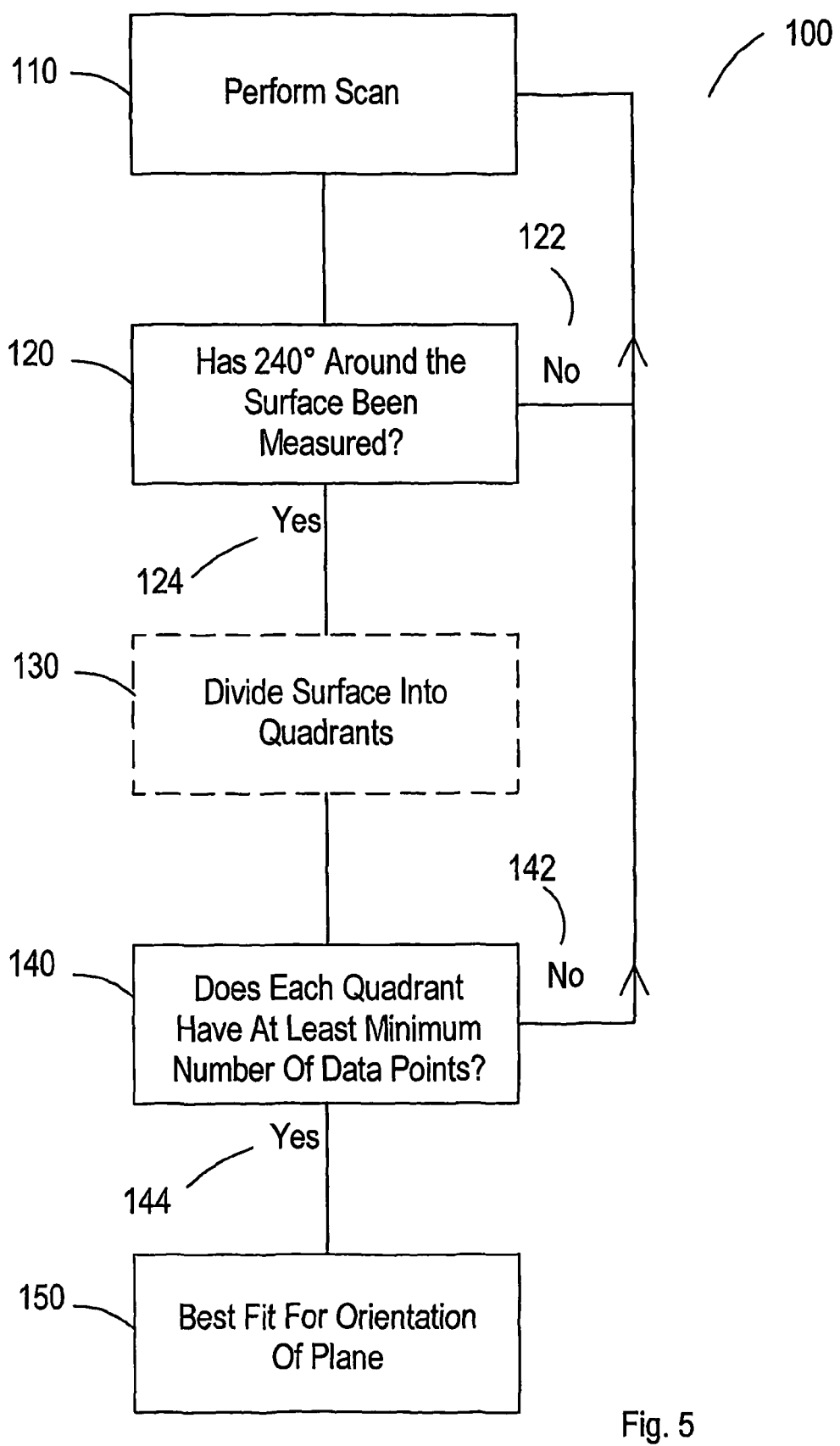
FIG. 5 is a flow diagram showing different steps according to an embodiment of the invention.

FIG. 5 shows a flow diagram 100 which details the steps involved in one embodiment of determining whether or not to accept the orientation information.

In this example, the probe automatically conducts a single scan of the upper surface and a sample. A single revolution consists of 1820 data points being taken by the probe tip.

Firstly, the scan 110 is conducted. Next, it is determined whether 240° around the surface of the sample holder has been conducted 120. If not, then the orientation scan is rejected 122. If the answer is yes, then the orientation information is accepted 124. Two-thirds (or 240°) around the surface is the minimum angular range required in order that a plane can be determined accurately. In this example, two-thirds around the surface means that 1220 data points have been collected.

In a next, optional step, the surface is divided into quadrants 130 and each quadrant is checked against a minimum number of data points 140. If any quadrant does not have the required minimum, the orientation information is rejected 142. If all the quadrants meet this requirement, we proceed 144 to the next step. The requirement that data is collected in each quadrant provides more accuracy and consistency than the requirement that two-thirds of a revolution is completed. This is because two-thirds of a revolution can include either three or four quadrants. As the inclusion of a minimum data set in each of four quadrants is statistically more accurate than the two-thirds of a revolution requirement, this is a preferred feature. In this example, a minimum data set for each quadrant is slightly less than half a whole quadrant data set i.e. 200 data points.

If this final, optional requirement is met, a best fit for the orientation of the plane is determined 150 using known mathematical techniques.

Additionally or alternatively, to ensure that any sample overhang is avoided in the calculation of the orientation of the plane of the upper surface, a maximum data set for each quadrant may be set. In this example, the number of data points per quadrant in a single revolution i.e. 455 data points is used as this limit. Again, the orientation information may be subject to x,y boundaries detailed above.

If the orientation information has been rejected, then a further scan is made whose data may be used instead of or as an addition to the data used in the rejected plane. Thus the orientation information may comprise data from a number of discrete scans. Furthermore, the orientation information may comprise data points from anywhere within the x,y boundary (if used) including from more than one revolution.

As an alternative to conducting a single scan, the datum and sample scans can be effectively carried out as one scan with a pause in between enabling automatic separation of the orientation data from the sample data. The sequence followed when deciding whether or not to accept the orientation information is the same.

Figure 6:
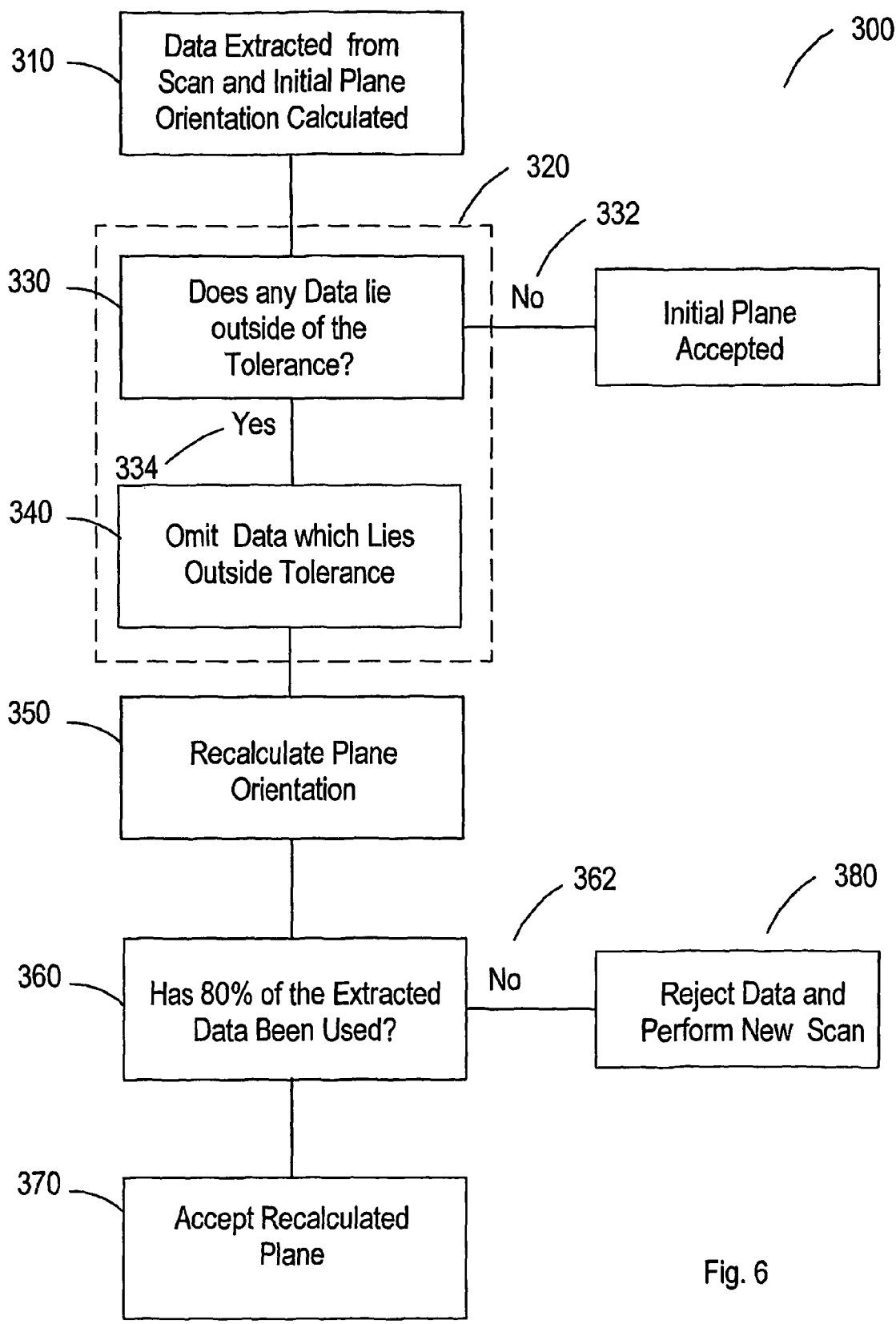
FIG. 6 is a flow diagram showing optimisation of the orientation plane.

FIG. 6 is a flow diagram 300 showing a preferred embodiment where the orientation data is optimised. Once the orientation data has been extracted from scan data and an initial plane orientation calculated 310, it is analysed 320 and measurement co-ordinates which are significantly different from the averaged plane are omitted.

The data is analysed 320 firstly to see is any of the data points lie outside the tolerance range 330 which is, for example, 15 µM. If no data is outside the tolerance range 330 then the initial calculation of the orientation of the plane is accepted 332. If there is data which exceeds the tolerance 334 then data points which are beyond a certain range of the initial calculated plane are omitted 340. This range can be the tolerance i.e. in this example 15 µM, or as is preferred less than this to ensure that the tolerance requirements are met, for example 10 µM. The orientation of the plane is recalculated 350.

As a safety check, it is preferred that the remaining data set which is used to recalculate the plane orientation comprises at least 80% of the extracted data 360 for the acceptance of the recalculated plane 370, otherwise the data is rejected and a further scan must be carried out 380.

Although in the examples given, the scanning device used has been a touch probe, the invention is not limited to such devices and non-contact probes such as optical scanning devices are also suitable for use with the invention.

The method according to the invention is suitable for use in any circumstances where it is required that the relationship of scanned data with respect to a plane of axis be known. Examples include the medical field and in particular the dental industry and the production of replacement teeth for use as an abutment or part of a bridge, where the scanned data is used to produce a replica tooth which must fit orientation wise with adjacent teeth in the bridge and mouth.

The invention claimed is:

1. A method of measurement by scanning comprising:
   providing a scanning measurement system having a sample holder and a relatively movable scanning device, the sample holder having a rotatable or longitudinal axis;
   using the scanning device to perform a scan of at least a part of an object located on the sample holder and of at least a portion of a surface of the sample holder to obtain measurement data;
   using at least a portion of the measurement data from the scan to establish an orientation of a plane of the sample holder and thereby establishing any misalignment or non-colinearity of the sample holder with respect to the rotatable or longitudinal axis; and
   interpreting at least a portion of the measurement data from the scan using the orientation of the plane of the sample holder in order to correct the measurement data for any established misalignment or non-colinearity of the sample holder with respect to the rotatable or longitudinal axis.

2. A method according to claim 1 wherein the orientation of the plane of the sample holder is established by defining a plane of the sample holder.

3. A method according to claim 2 wherein the plane of the sample holder in which orientation is established is limited by boundaries.

4. A method according to claim 1 wherein the orientation of the plane of the sample holder is established by extracting at least three measurements.

5. A method according to claim 1 wherein the orientation of the plane of the sample holder is established by extracting data for at least 240° around the surface of the sample holder.

6. A method according to claim 1 wherein the orientation of the plane of the sample holder is established by measuring during a single process.

7. A method according to claim 1 wherein the orientation of the plane of the sample holder is established by measuring during more than one discrete processes.

8. A method according to claim 1 wherein the orientation of the plane of the sample holder is established within a defined vertical envelope with respect to the sample holder.

9. The method of scanning according to claim 1 wherein the scan of at least part of the object and the scan of at least a portion of the sample holder are conducted as a single scan.

10. A method of measurement by scanning comprising:
    providing a scanning measurement system having a sample holder and a relatively movable scanning device, the sample holder having a rotatable or longitudinal axis;
    performing a datum scan with the scanning device to obtain measurement data for establishing any misalignment or non-colinearity of the sample holder with respect to the rotatable or longitudinal axis;
    performing a sample scan with the scanning device of a sample to obtain measurement data of the sample; and
    interpreting the measurement data of the sample from the sample scan using any misalignment or non-colinearity data obtained from the datum scan in order to correct the measurement data of the sample for any established misalignment or non-colinearity of the sample holder;
    wherein the scanning measurement system automatically carries out the datum scan and the sample scan.

11. The method of scanning according to claim 10 wherein the datum scan and the sample scan are conducted as a single scan.

12. A method of measurement by scanning comprising:
providing a scanning measurement system having a sample holder and a relatively movable scanning device, the sample holder having a rotatable or longitudinal axis;
performing a datum scan with the scanning device to obtain measurement data for establishing any misalignment or non-colinearity of the sample holder with respect to the rotatable or longitudinal axis;
performing a sample scan with the scanning device of a sample to obtain measurement data of the sample; and
interpreting data from the sample scan using any established misalignment or non-colinearity data from the datum scan in order to correct the measurement data of the sample for any established misalignment or non-colinearity of the sample holder;
wherein both the datum scan and sample scan are carried out effectively as one scan.

* * * * *